US006036719A

United States Patent [19]

Meilus

[11] Patent Number: 6,036,719

[45] Date of Patent: Mar. 14, 2000

[54] MUSCULAR THERAPY TREATMENT APPARATUS FOR SPINE MUSCLES

[76] Inventor: Algis Albert Meilus, 331 N. Tessier-Dr., St. Pete Beach, Fla. 33706

[21] Appl. No.: 09/189,164

[22] Filed: Nov. 9, 1998

Related U.S. Application Data

[63] Continuation-in-part of application No. 08/854,843, May 12, 1997, abandoned.

[51] Int. Cl.[7] .......... A61F 5/00

[52] U.S. Cl. .......... 606/204; 606/240; 601/134

[58] Field of Search .......... 606/204, 237, 606/238, 240, 241, 242, 201; 601/134

[56] References Cited

U.S. PATENT DOCUMENTS

| | | | |
|---|---|---|---|
| 712,375 | 10/1902 | Hartford | 606/204 |
| 1,746,080 | 2/1930 | Hamilton | 606/237 |
| 1,833,426 | 11/1931 | Knudson | 606/240 |
| 2,159,654 | 5/1939 | Catlin | 606/240 |
| 4,230,099 | 10/1980 | Richardson | 606/240 |

FOREIGN PATENT DOCUMENTS

| | | |
|---|---|---|
| 1 132 190 | 3/1957 | France . |
| 2003319 | 11/1993 | Russian Federation . |

*Primary Examiner*—Michael Buiz
*Assistant Examiner*—David O. Reip
*Attorney, Agent, or Firm*—Dorothy S. Morse

[57] ABSTRACT

A muscular therapy treatment apparatus for patient self-treatment in applying concentrated pressure to deep muscle attachments in the lamina groove on either side of the spinous processes of spine vertebrae to relax and lengthen the muscles therein and cause vertebrae alignment without the forcing of bone. Each embodiment of the apparatus has a rigid planar base support and a treatment member depending upwardly therefrom with a pair of sharp edges on its curved upper peripheral surface. A groove separates the sharp edges and receives the spinous processus of vertebrae when a patient becomes positioned on top of or against the peripheral surface during use. The groove can have straight interior walls intersecting at an angle between 60° to 70°, or it can have an arcuate configuration. The present invention discloses a variety of partial-spine treatment embodiments, as well as a whole-spine treatment embodiment that allows all of the muscles flanking the spinal column to be treated at once. The peripheral surfaces of the embodiments used for the cervical and lumbar regions of the spine conform to the natural concave curvature of those regions. However, it is preferred that the curved peripheral surface of the thoracic region treatment embodiments have a configuration slightly reversing the curvature of that region in a prone patient. Also, in the whole-spine treatment apparatus, approximately one-third of the base support, specifically that in the lumbar region, has a raised thickness dimension.

20 Claims, 4 Drawing Sheets

FIG. 1
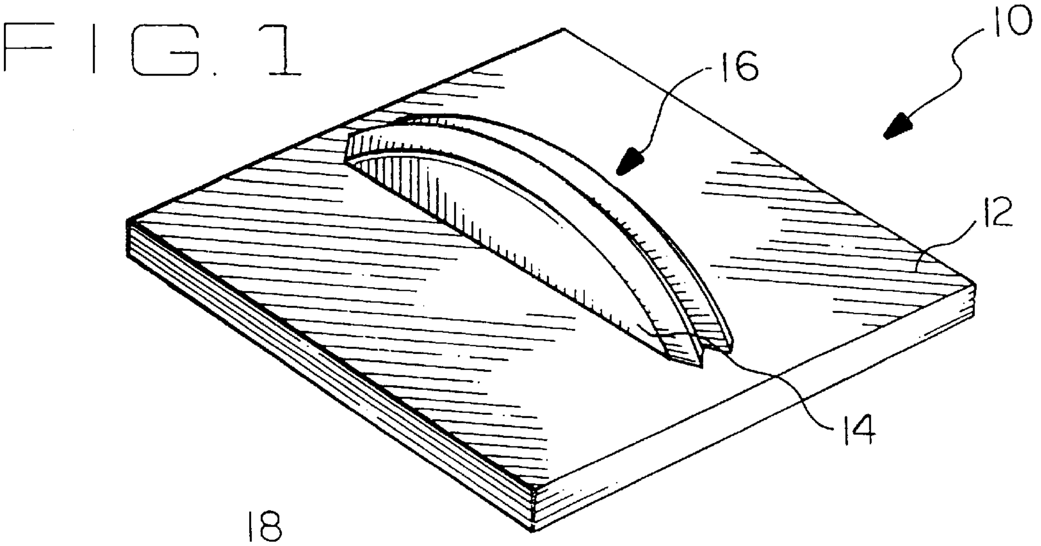
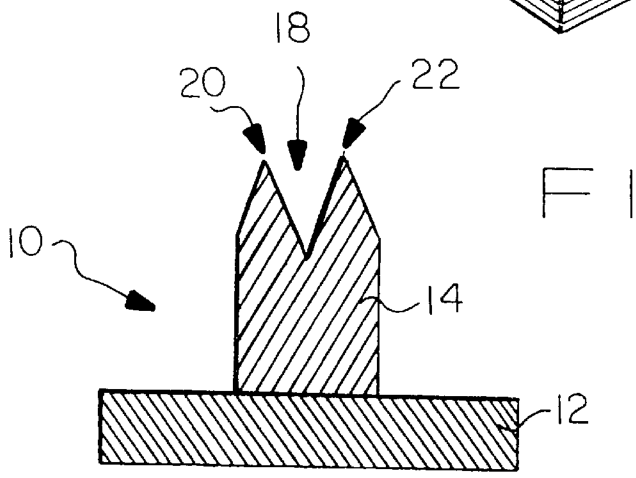
FIG. 2
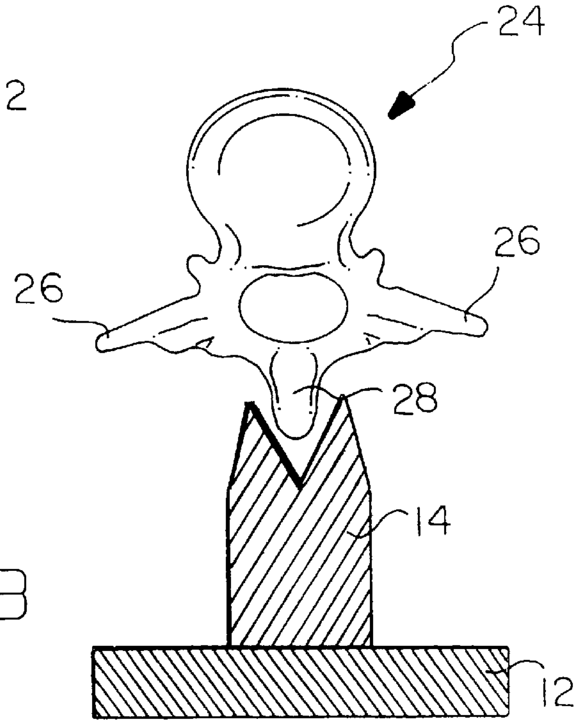
FIG. 3

FIG. 7
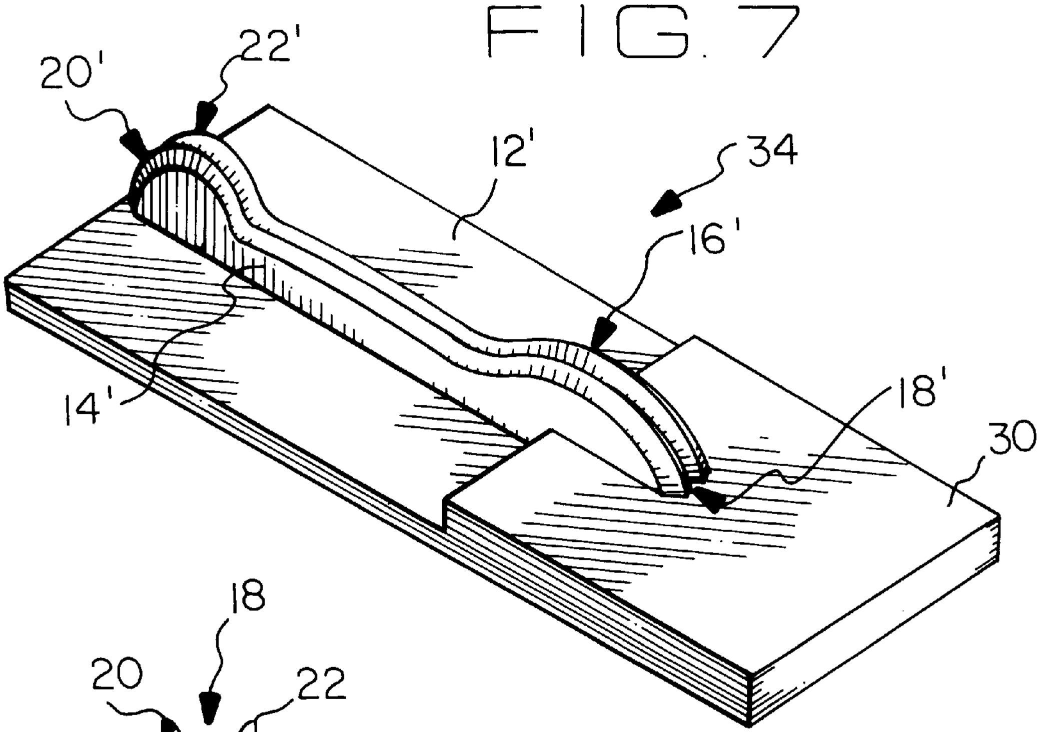
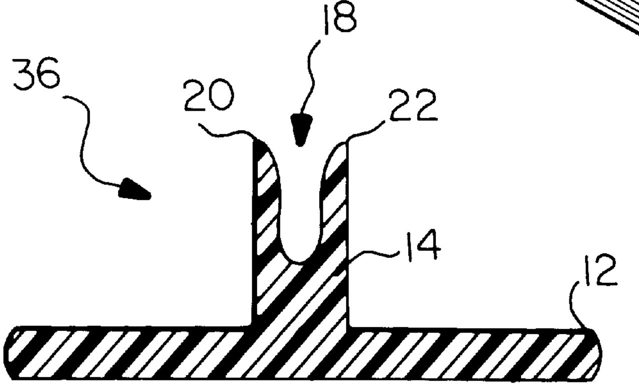
FIG. 8
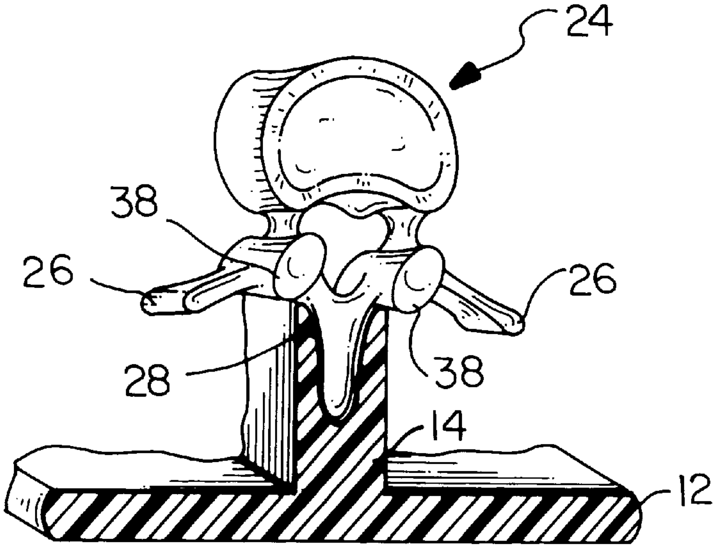
FIG. 9

MUSCULAR THERAPY TREATMENT APPARATUS FOR SPINE MUSCLES

This is a continuation-in-part of patent application Ser. No. 08/854,843 filed on May 12, 1997, now abandoned.

BACKGROUND OF THE INVENTION

The present invention relates to muscular therapy treatments wherein concentrated pressure is applied to relax and lengthen muscle attachments, even those deeply positioned under other tissue, as opposed to massage therapy wherein surface muscles generally undergo treatment. The present invention provides several embodiments of devices that would be alternatively used for muscular therapy treatment of muscles associated with the spine, including both partial-spine and whole-spine apparatus designed for patient self-treatment, and a method for their use. Each embodiment has a treatment member with a curved peripheral surface upwardly depending from a planar base support and a pair of sharp upper edges spaced-apart on the peripheral surface to form a central groove, the sharp edges being configured and strategically positioned to apply deep concentrated pressure to muscles attached in the lamina groove on either side of the spinous processes of vertebrae in a patient who is either in a supine position on top of the apparatus, such as during use of either the whole-spine or partial-spine embodiments, or who is pressing against a partial-spine apparatus when sitting in a chair having a back member or adjacent to a wall or other type of upright rigid support surface. The groove can be formed either by sharp edges that are separated by straight interior walls set apart at an angle between approximately 60° and 70°, or the interior of the groove can have an arcuate configuration similar to and slightly larger than the shape of the spinous processus it is intended to receive. In each partial-spine apparatus the base support is both longer and wider than the treatment member, with the treatment member being positioned centrally upon the base support to enhance its stability during use. In the whole-spine apparatus the base support is also both longer and wider than the treatment member, with the treatment member being centrally positioned widthwise on the base support, but with the treatment member being positioned lengthwise so that its cervical end is set adjacent to the upper end of the base support and the treatment member extends lengthwise across approximately three-fourths of the length of the base support. Also, the lower end of the base support, comprising a portion approximately one-third of the total base support length, is made to have a greater thickness dimension than that of the remainder of the base support, with the thicker portion of the base support extending from the approximate center of the lumbar portion of the treatment member and beyond its lumbar end, the thicker portion of the base support positioning the patient's lower back optimally for effective pressure application to muscle attachments in the lamina groove on either side of the spinous processes of the patient's lumbar vertebrae. It has been determined that most of the excess contraction in a muscle is found near to its attachment points, and not centrally in the belly of the muscle. The prolonged and repeated concentrated pressure applied by the apparatus of the present invention during self-treatment of patient muscle attachments in the lamina grooves, reaches contracted muscles deeply positioned underneath multiple layers of tissue and causes them to lengthen. As a result of such lengthening, treated patients are provided with relief from any muscular tension and pain that might have been caused by excess contraction within the attachments of the treated muscles.

Also, such lengthening would allow bones formerly misaligned by such excess contraction to automatically seek their proper operating positions.

BACKGROUND OF THE INVENTION

Description of the Prior Art

People commonly experience musculoskeletal pain and muscular tension, the origin of which can be traced to a variety of sources, including but not limited to repetitive sports activity, other strenuous physical activity, accidents, poor posture, and medical conditions. Such pain is routinely treated by a variety of procedures which include the use of anti-inflammatory drugs, narcotic medications, thermal devices to raise or lower the temperature of affected tissues, electric stimulation, ultrasound, physical therapy, and massage therapy. However, while use of these treatment procedures can provide temporary relief from adverse symptoms and related limitations in mobility, such procedures are usually not effective in relieving the cause of the symptoms and the pain and limited mobility ultimately return. Also, while drugs and medications provide temporary relief, they can induce adverse side affects in some patients.

Muscular therapy is an alternative to the above-mentioned treatments in relief of a patient's musculoskeletal pain and tension. Unlike massage therapy which superficially treats the muscle itself, or physical therapy which works to strengthen weak spots, muscular therapy is the practice of repeatedly applying concentrated pressure to a muscle, particularly muscle attachments where it has been demonstrated that the majority of excess muscle contraction occurs, to release from the muscle any build-up of lactic acid and other metabolic by-products resulting from strenuous exercise, spasm, and/or tension. Upon such release, normal blood flow is restored to a muscle, and any pain or tension previously associated with the muscle becomes diminished. As pressure is applied gradually and specifically to the point of muscle spasm, sometimes the size of a small pea, three changes occur. First the muscle tissue lengthens, which is observable under a microscope. Second, the electrical activity is reduced in the nerves that innervate the muscles in the treated area, a change which is measurable by EMG units, such as those typically used for biofeedback. Third, three acids are released, lactic acid, carbonic acid, and hyaluronic acid which result in the sting and discomfort felt by the patient during the application of the concentrated pressure. As this therapeutic process continues, the muscle tissues soften, the discomfort diminishes, and when all of the acid is removed from the muscle, one hundred pounds or more of pressure can usually be applied to the muscle with no discomfort. Muscular therapy takes an engineering approach to treating the body by viewing it as a series of cables and fulcrums. Through identification of the muscles operating different filcrums within the body during a repeated activity, diagnosis, treatment, and reduction of pain and any limited mobility caused by the repeated activity can be provided through the use of physics and the repetitive application of concentrated pressure to specific muscles one-at-a-time to lengthen them so that associated joints can move with less restriction. Relief provided by muscular therapy is often immediate and allows the quick resumption of activity. Preventative muscular therapy and self-treatment can prevent problems from recurring. Also, with continued muscular therapy, it has been documented that muscles have a faster response time, greater stamina, more leverage, and both increased power and accuracy. Further, people with a skewed center of gravity, both disease-related and that due to poor posture, can achieve better balance through muscular therapy. In addition, it has been shown that the repetitive application of concentrated pressure to injured tissue, in addition to relieving pain and enhancing blood circulation, desensitizes it and helps to speed the maturation of scars.

Traditionally, muscular therapy treatments have been performed manually by therapists using their fingers, hands, elbows, and the like, to press down on muscles to stretch them and enhance circulation therein. Similar procedures involve cranial-sacral therapy wherein a therapist's hands have been used to separate a space between the base of the skull and the first vertebra so that the dural tube covering the spinal column can be stretched and tractioned from the base of the skull to the sacrum. Muscular therapy is physically demanding on a therapist since in performing certain treatment procedures, such as when an attempt is made to loosen back muscles, the muscular therapist is required to apply pressures which can exceed one-hundred pounds of pressure. Therefore, as a work day progresses it is common for muscular therapists to tire, and treatments given later in the day may not be uniform. Also as a consequence of the physical demands of their profession, muscular therapists must sometimes to limit the amount of time they manually perform tissue manipulation. Generally patients have been prevented from self-treatment of muscles attached to their spine by hand manipulation due to the awkward angles required to reach such muscles. The present invention provides a means for patient self-treatment of muscles attached in the lamina groove on either side of the spinous processes of their vertebrae so that deep, concentrated pressure can be applied to the spinal muscle attachments which duplicates the type of concentrated pressure that would be applied manually to such muscles by a muscular therapist's hands. The present invention does not tire during a day's work and will consistently apply uniform pressures at any time of the day. While it is known to have devices which support the spine and apply soothing, superficial pressure to muscles, or devices which stretch surface muscles associated with the spine, it is not known to have a treatment apparatus for muscles attached in the lamina grooves on either side of the spinous processes of human vertebrae which has all of the advantages of the present invention.

The prior art thought to be most closely associated with the present invention are the inventions disclosed in U.S. Pat. No. 4,230,099 to Richardson (1980), Russian Patent RU2003319-C1 to Ivanova, and French Patent 1.132.190 (1957). The Richardson invention discloses a device upon which a person would lie for aligning the bones in his or her spine. The Richardson invention comprises an essentially planar base member with two elongated ridge members in substantially parallel position, spaced apart from one another, and upwardly depending from the base member. Each ridge member has a convex curve near one end substantially corresponding to the natural lumbar curve of a human spine, a concave curve adjacent to the convex curve substantially corresponding to the natural thoracic curve of a human spine, and a convex curve adjacent to its other end slightly less than the normal cervical curve of a human spine. The design of the Richardson invention is based upon accupressure and its ridge members each have a rounded configuration to distribute forces applied to muscles on either side of the spine that are larger and broader than those targeted by the present invention. In contrast, one embodiment of the present invention has a pair of sharp upper edges which are spaced apart by a groove having straight interior walls set apart at an angle between approximately 60° and 70° to apply deep concentrated pressure to muscles on either side of the spine to the point of discomfort. A second embodiment of the present invention would employ an arcuate groove configured to closely resemble the curvature of the spinous processus it is intended to receive. Another distinction between the Richardson invention and the present invention is that the Richardson invention has a central groove between its ridge members which forces it to avoid placing pressure on the spinous processus, instead allowing it to direct its applied pressure toward the bony part of the spine vertebrae called the transverse process. Conversely, the present invention places pressure in the lamina groove immediately adjacent to the spinous processus, a concave area in the spine that has up to seven layers of muscle attaching to it. Its sharp edges apply concentrated pressures to deeply reach even the lowermost of the seven layers of muscle within the lamina groove. The Richardson invention is configured to force bones into proper alignment while the present invention is configured to focus pressure on muscles to lengthen them so that bones may seek proper alignment without the interfering muscle contraction which formerly affected them. Thus, during use the present invention is positioned for muscular treatment close to the spinous processus where muscle attachments are located and consequently where much of the muscle tension is found. FIG. 5 of the Richardson disclosure shows the Richardson device supporting the transverse process. In contrast, FIG. 9 of the present invention shows the sharp upper edges of its treatment member positioned to apply much higher pounds per square inch pressures to the seven layers of muscle in the lamina groove, the higher and more precisely applied pressures allowing it to cause more effective vertical alignment than is possible with the Richardson invention. Vertical alignment of bone achieved by the Richardson invention is accomplished by it relaxing the surface muscles on either side of the vertebrae and then placing pressure on the outside of each vertebrae to force the bones into place. In contrast, the present invention is faster and more effective in achieving vertical alignment since it allows the bones automatically to move back into place once all of the deep muscles have been relaxed, deep muscles that the Richardson invention due to its configuration would be unable to reach. Also, the whole-spine embodiment of the present invention has a thickened lumbar base support which is not taught by the Richardson. Merely sharpening the edges of the Richardson invention would not provide all of the treatment advantages of the present invention for applying concentrated pressure to deep muscle attachments within the lamina groove on either side of the spinous processes of a patient.

The Ivanova invention also discloses a spinal column treatment device which has a pair of prismatic projections joined to each other by a curved surface for treatment of thoracic and lumbar regions of a spinal column. An additional pair of projections are positioned perpendicular to the prismatic projections so that the Ivanova invention can been used on its side for additional treatment of the cervical region of the spinal column. The upper surfaces of all projections are rounded, in contrast to the thin, sharp upper edges of the treatment member of the present invention which are spaced apart by either a straight-walled groove with interior walls set apart at angle between approximately 60° and 70°, or an arcuate groove closely resembling the configuration of the spinous processus it is intended to receive, to apply deep concentrated pressure to muscles on either side of the spinous processus to the point of discomfort. Similar to the function of the Richardson invention, the Ivanova invention would distribute forces applied to larger and broader surface muscles attached to the spine which are not targeted by the present invention. Between its ridge members the Ivanova invention also has a central groove similar to that in the Richardson invention. The groove causes the Ivanova invention to avoid placing pressure on the spinous processus and direct its applied pressure toward the laterally positioned bony parts of spine vertebrae called the transverse processes. Dissimilar to the present invention, the Ivanova invention does not place pressure in the lamina groove immediately adjacent to the spinous processus, nor are its rounded upper edges able to reach and treat the lowermost of the seven layers of muscle within the lamina groove. In contrast, the present invention is positioned during use for muscular therapy treatment of muscle attachments close to the spinous processus which consequently is where much of the muscle tension is located. The higher and more precise muscular treatment pressures applied by the present invention allow it to cause faster and more effective vertical vertebrae alignment than is possible with the Ivanova invention, and result in the patient's bones automatically moving back into proper position once all of the deep muscles have been relaxed, deep muscles that the Ivanova invention would also be unable to reach. Thus the Ivanova invention applies force to bone to move it into a desired position, while the present invention moves bone by lengthening the muscle attached to it by applying high levels of concentrated pressure to it to the point of discomfort, pressure sometimes exceeding one-hundred pounds of pressure.

The invention in French Patent '190 discloses two upstanding members with a groove therebetween being supported by a planar base member. The upper surfaces of the two upstanding members are each convex to correspond to the concave curvature of the lumbar-sacral area of the spine. The upstanding members extend substantially the full length of the base member and are made from a flexible material, such as foam. It is contemplated that the invention of French Patent '190 is particularly useful for the treatment of scoliosis. However, as a result of its flexible upstanding members, the invention of French Patent '190 would be ineffective in applying the deep, concentrated pressures required to reach and treat the lowermost of the seven layers of muscle within the lamina groove. It is not known to have a muscular therapy device designed for patient self-treatment which has a convex treatment member upwardly depending from a planar base support, a pair of sharp upper edges on the curved peripheral surface of its treatment member separated by an essentially V-shaped groove approximately one-half inch deep and one-half inch across at its greatest width so that the sharp edges are set apart from one another by straight interior walls spaced apart at an approximate 60° to 70° angle or a groove having an arcuate configuration which closely resembles that of the spinous processus it is intended to receive, for use in the application of deep concentrated pressure to muscles attached in the lamina grooves on either side of the spinous processes of a patient's vertebrae so that contracted muscles beneath multiple layers of tissue can be caused to lengthen and provide rapid vertebral alignment without any forcing of bone, as well as provide treated patients with relief from muscular tension and pain, and the limited mobility caused by prior excess contraction.

SUMMARY OF THE INVENTION

The primary object of the present invention is to provide a patient self-treatment device that duplicates the type of deep concentrated pressures applied manually by the hands of muscular therapists to muscles attached in the lamina groove on either side of the spinous processes of human vertebrae to reduce the physical burdens placed upon muscular therapists in applying the high pressures exceeding one hundred pounds of pressure necessary to effectively treat such muscles. It is also an object of the present invention to provide a patient with a single self-treatment device which can treat all of the muscles that attach in the lamina groove of the cervical and thoracic portions of the spine, as well as the lumbar region of the spine. A further object of the present invention is to provide a patient self-treatment device which duplicates manual muscular therapy treatments for the muscles attached in the lamina groove on either side of the spinous processus, and in replacing the hands of the human therapist which can become tired as a work day progresses, the present invention would offer more consistent and uniform patient treatments. It is also an object of the present invention to provide a patient self-treatment device to duplicate manual muscular therapy treatments for muscles attached in the lamina groove on either side of the spinous processes of human vertebrae that is made from materials which are low in cost, lightweight and convenient to use, and easily cleaned.

As described herein, properly manufactured and used, the present invention would provide a compact, easy-to-use treatment apparatus for muscles attached in the lamina groove on either side of the spinous processes of human vertebrae to relax and lengthen such muscles and thereby permit the vertebrae to automatically move back into normal operating positions as the muscles relax, without any forcing of bone. It is important to note that the present invention does not apply force to bones to coax them into place. Bone movement only occurs as the muscles in the lamina groove on either side of the spinous processes are relaxed. The mere act of lying atop the present invention often provides an instantaneous adjustment or a "popping" back into place of vertebrae that were out of position prior to treatment, simply as a result of muscles relaxing and lengthening. The present invention can be built from a variety of inexpensive materials, and since it has a simple structure which is easy to manufacture, it could be made readily affordable to muscular therapists for widespread application, as well as for widespread self-treatment use by patients. Since it is a rigid device, it would not tire and could provide more consistent and uniform treatment than the hands of a human therapist. One preferred embodiment of the present invention contemplates its base support and treatment member being made from plastics through molded construction as a one piece unit which would be light in weight and easy to clean between patient uses. The pair of sharp upper edges on the curved peripheral surface of the treatment member are spaced apart at a distance of approximately one-half of an inch to allow the treatment member to apply high, concentrated pressures to muscles in the lamina groove of the spinous processus of a supine patient, sufficient pressure to reach muscles deeply positioned under multiple layers of muscle. The groove between the sharp edges can either have straight interior walls set apart at an angle approximately between 60° and 70° or an arcuate configuration closely resembling that of the spinous processus it is intended to receive. Known prior art devices distribute applied forces and are not able to reach and treat the deep muscles in the lamina groove to lengthen them and provide a patient increased mobility and relief from tension and pain, among other benefits. In the present invention it is contemplated to have both a whole-spine treatment apparatus for simultaneous collective treatment of the cervical, thoracic, and lumbar areas of the spine, as well as individual partial-spine treatment apparatus for different areas of the spine.

The description herein provides preferred embodiments of the present invention, but should not be construed as limiting the scope of the muscular therapy invention. For example, variations in the type of material from which the base support is made as long as the material is sufficiently rigid to perform its function and easily cleaned, the type of material from which the upwardly depending treatment member is made, the thickness of the base support, and the process by which the base support and the treatment member are joined, other than those shown and described herein, can be incorporated into the present invention. Thus the scope of the present invention should be determined by the appended claims and their legal equivalents, rather than the examples given.

BRIEF DESCRIPTION OF THE DRAWINGS

FIG. 1 is a perspective view of a first embodiment of the present invention which is a partial-spine treatment device used for muscular therapy treatment in either the cervical, thoracic, or lumbar areas of the spine, the area targeted for treatment being determined by the height, width, and length dimensions of its upright treatment member.

FIG. 2 is a sectional view of the first embodiment with an upright treatment member having a pair of sharp edges separated by a central groove with straight interior walls set apart at an angle between approximately 60° and 70°.

FIG. 3 is a sectional view of the first embodiment of the present invention placed in its treatment position adjacent to the spinous processus of a vertebra with the sharp edges adjacent to its groove directed toward the lamina groove located on either side of the spinous processus, between the vertebra's spinous processus and each transverse processus.

FIG. 7 is a perspective view of a second embodiment of the present invention which is a whole-spine treatment device used for muscular therapy treatment in the collective cervical, thoracic, and lumbar areas of the spine, with the upper end of its treatment member positioned adjacent to the upper edge of the base support, and in which approximately the lower one-third of the length of its base support has a thickness dimension greater than that of the remainder of the base support.

FIG. 8 is a sectional view of a third embodiment of the present invention for partial-spine treatment with a groove having a partially arcuate configuration separating its sharp edges.

FIG. 9 is a sectional view of the third embodiment of the present invention placed in its treatment position adjacent to the spinous processus of a vertebra with the configuration of the groove closely resembling, but slightly larger than, the configuration of the spinous processus of the vertebra.

DETAILED DESCRIPTION OF PREFERRED EMBODIMENTS

Figure 6:
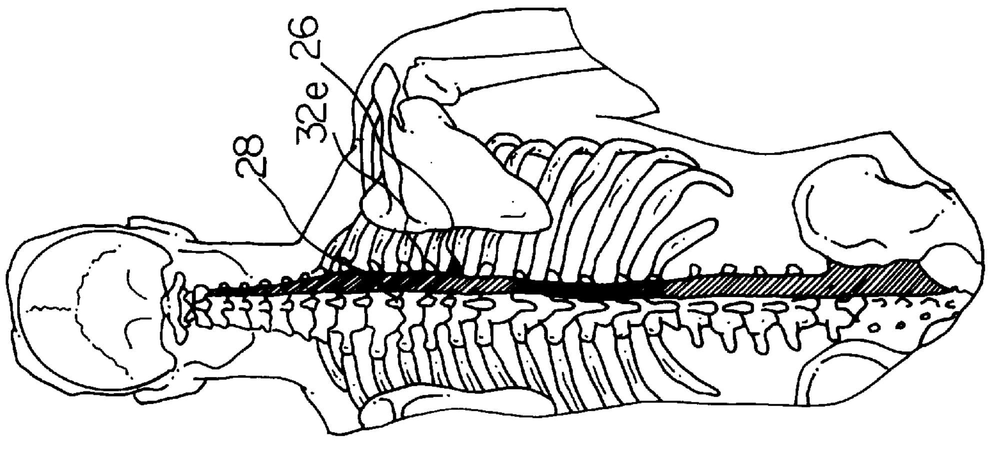
FIG. 6 is a rear view of multifidi rotatores muscles attached within the lamina groove on one side of the spinous processes of human vertebrae.

FIG. 1 shows a first embodiment 10 of the present invention for partial-spine treatment. Although FIG. 1 actually shows an embodiment 10 for treatment of the cervical areas of a human spine (not shown), partial-spine embodiments for treatment of thoracic and lumbar areas of a human spine would have a similar construction, with the exception that each partial-spine embodiment for treatment of a thoracic or lumbar area of the spine would have a front configuration resembling that shown in FIG. 14 and FIG. 15, respectively. In FIG. 1, partial-spine treatment embodiment 10 is shown to have a rigid planar base support 12 and a convex treatment member 14 upwardly depending from the central portion of base support 12. Treatment member 14 is approximately centered against base support 12 in both length and width directions. The configuration and dimension of base support 12 is not critical to the present invention as long as it has sufficient dimension to securely position and stabilize treatment member 14 during muscular therapy use. Also, the material from which base support 12 is made is not critical to the present invention as long as it has sufficient rigidity to support the weight of a patient (not shown) positioned on top of treatment member 14. However, in the first preferred embodiment 10 for treatment of the cervical area of a human spine it is contemplated for base support 12 to have a square configuration with its sides each having a minimum length of approximately eight inches. Correspondingly, treatment member 14 would be expected to have a length dimension of approximately six inches and a height dimension of approximately four inches. Other embodiments 10 for cervical area treatment can be made with proportionately smaller or larger length and height dimensions to suit individual needs. Although not critical to the present invention, it is contemplated for base support 12 and treatment member 14 to be made from plastic materials which are lightweight and easily cleaned after patient use, and for base support 12 and treatment member 14 to be made as a single unit from molded construction. In the alternative, although not shown, treatment member 14 could be secured to base support 12 by any conventional means which strongly fixes one to the other during use, such as through the use of adhesives or bonding agents. FIG. 1 also shows treatment member 14 having a curved peripheral surface 16.

In partial-spine treatment embodiment 10 it is contemplated for curved peripheral surface 16 to have a fixed radius of curvature corresponding to the radius of curvature of the concave portion of a human cervical region (not shown). Similarly, in partial-spine embodiments 10 for treatment of a lumbar region (not shown), or a thoracic region (not shown), it is contemplated for curved peripheral surface 16 to have a fixed radius of curvature corresponding to the radius of curvature of the respective region of the spine. The shape of curved peripheral surface 16 for embodiments 10 used in treatment of the thoracic region can also be designed to slightly reverse the curve of the thoracic spine (not shown) when a patient lies thereupon in a supine position. As stated above, the length dimension of treatment member 14 is not critical and it is contemplated for different partial-spine treatment embodiments 10 of the present invention to comprise treatment members 14 having different lengths. The chosen length of treatment member 14 will depend upon several factors, including the stature of the person for whom treatment is desired, whether an entire spinal region is to be treated at once, or whether it is determined to be more desirable to treat a spinal region in several successive treatments with a smaller treatment member 14. It is also contemplated for the partial-spine treatment devices of the present invention, such as partial-spine treatment embodiment 10 shown in FIG. 1, to be either used by a patient lying in a supine position thereon or sitting in a chair (not shown), or leaning against some other type of rigid support surface (not shown).

Similarly, FIG. 2, shows partial-spine treatment embodiment 10 comprising base support 12 and treatment member 14 upwardly depending from the central portion of base support 12. FIG. 2 also shows treatment member 14 having a groove 18 formed in its distal portion, with the sharp edges, identified by numbers 20 and 22, being positioned on either side of groove 18. In embodiment 10 it is contemplated for groove 18 to have straight interior walls set apart at an angle between approximately 60° and 70°. Thus, when the spine of a patient's cervical region, thoracic region, or lumbar region (not shown) is positioned parallel to and aligned with groove 18 in treatment member 14, spaced apart sharp edges 20 and 22 become placed against muscles, such as muscles 32*a–e* shown in FIGS. 4–6, which are attached in the lamina groove on the opposite sides of the spinous processes of the patient's vertebrae to apply deep concentrated pressure to those muscles to lengthen them and thereby relieve pain previously associated with excess contraction therein. As a patient lies upon curved peripheral surface 16 in a supine position, or sits pressing his or her back against it, the spinous processus of each vertebrae becomes suspended within groove 18 which allows sharp edges 20 and 22 to perform the function of single-edged sharp, beveled pressure bars (not shown), developed by the inventor herein and commonly used by muscular therapists (not shown) to apply pressure manually to a patient's spinal muscles, such as muscles 32*a*–32*e* in FIGS. 4–6. It is contemplated during construction of partial-spine treatment embodiment 10 for sharp edges 20 and 22 to be filed or otherwise configured so that they are sufficiently sharp and can apply over one-hundred pounds of pressure to a patient's skin, yet not be sharp enough to pierce it. FIG. 3 shows treatment member 14 depending upwardly from base support 12 and positioned centrally beneath the spinous processus 28 of a thoracic vertebra 24. In contrast, prior art inventions (not shown) function to distribute pressure across an area that includes the two transverse processes 26 of thoracic vertebra 24.

Figure 5:
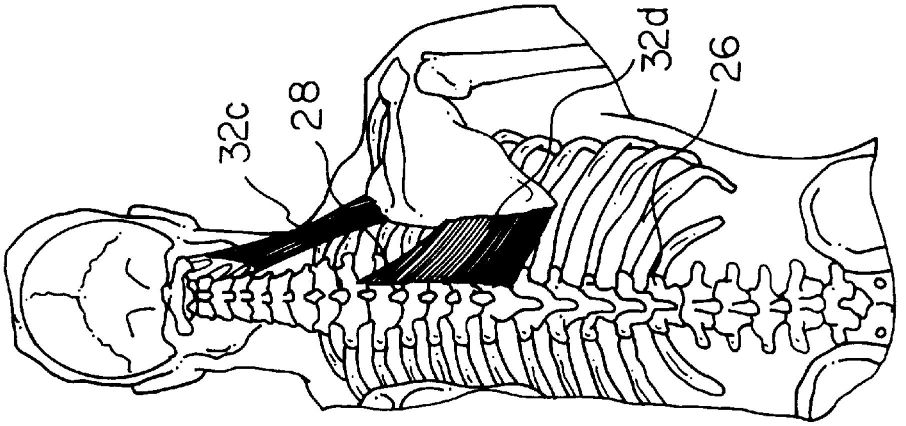
FIG. 5 is a rear view of rhomboid muscles attached within the lamina groove on one side of the spinous processes of human vertebrae.
Figure 4:
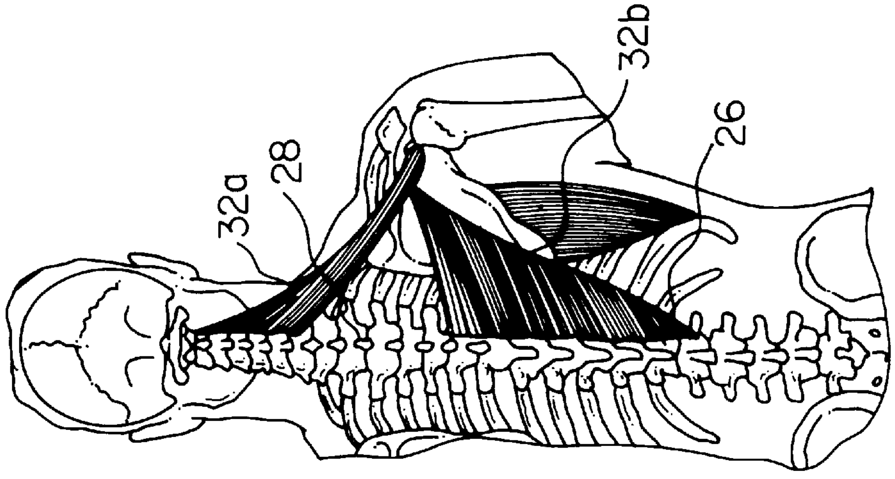
FIG. 4 is a rear view of trapezius muscles attached within the lamina groove on one side of the spinous processes of human vertebrae.

FIGS. 4, 5, and 6 show muscles 32*a*–32*e* having attachments in the lamina groove on either side of the spinous processes 28 of a human spine, the attachments being located between the spinous processus 28 and the transverse processus 26 on one side of a human back. For simplicity of illustration, muscles are shown attached only on one side of the spinous processes 28. Muscles 32*a*–32*e* are only examples of several of the muscles comprising the seven layers of muscle attachments (not shown) targeted by sharp edges 20 and 22 in their application of more than 100 pounds of pressure to release excess contraction therein even in the most deeply positioned of the muscle attachments. FIG. 4 shows trapezius muscles as numbers 32*a* and 32*b* each having one of its ends attached in the lamina groove between the spinous processes 28 and the transverse processes 26 in the cervical and thoracic areas of a human spine. FIG. 5 shows rhomboid muscles 32*c* and 32*d* each having one of its ends attached in the lamina groove between the spinous processes 28 and the transverse processes 28 in the cervical and upper thoracic areas of a human spine. Further, FIG. 6 shows multifidi rotatores muscles 32*e* each having one of its ends attached in the lamina groove between the spinous processes 28 and the transverse processes 28 of the cervical, thoracic, and lumbar areas of a human spine.

FIG. 7 shows a second embodiment 34 of the present invention which is used for whole-spine treatment of muscle attachments in the combined cervical, thoracic, and lumbar areas of a human spine while a person is supine thereupon. Whole-spine treatment embodiment 34 has a rigid, planar base support 12' and a grooved treatment member 14'. FIG. 7 shows the longitudinal extent of treatment member 14' to be substantially equal to the combined longitudinal extent of three combined partial-spine treatment embodiments 10, to include one for the cervical area, one for the thoracic region, and one for the lumbar region of a patient's spine. Curved peripheral edge 16' for whole-spine treatment embodiment 34 is shaped to substantially conform to the concave configuration of a combined cervical region, thoracic region, and lumbar region of a human spine. More particularly, the respective shapes of the cervical and lumbar regions of whole-spine treatment embodiment 34 conform to the corresponding concave configuration of the cervical and lumbar regions of the human body, but in a preferred embodiment, the shape of the thoracic region of whole-spine treatment embodiment 34 would slightly reverse the curvature of the thoracic region of a patient lying supine thereupon. However, following the thoracic curve of a human spine is also within the scope of this invention. FIG. 7 also shows base support 12' having a raised portion 30 at the end of base support 12' for use in treating the lumbar region of a spine. Raised portion 30 comprises approximately one-third of the length of base support 12' and raises the lumbar region of a patient so that curved peripheral surface 16' can more effectively apply deep concentrated pressure to those of the patient's muscles attached to the lumbar region of the patient's spine, such as muscles 32*e* shown in FIG. 6. In whole-spine treatment embodiment 34, base support 12' is both longer and wider than treatment member 14', with treatment member 14' being centrally positioned widthwise on base support 12'. In contrast, treatment member 14' is not centered lengthwise on base support 12', but instead is positioned lengthwise so that its cervical end is set adjacent to the upper end of base support 12' and treatment member 14' extends lengthwise across approximately three-fourths of the length of base support 12'. Also, raised portion 30 extends from the approximate center of the lumbar portion of treatment member 14' and beyond its lumbar end. FIG. 7 also shows groove 18' positioned between sharp edges 20' and 22'. It is contemplated in the whole-spine embodiment 34 for groove 18' to have straight interior walls set apart at an approximate angle between 60° and 70°, or to have an arcuate interior surface as described below for third embodiment 36. It is further contemplated for the sharp edges 20' and 22' of the whole-spine embodiment 34 to be filed or otherwise adapted so as to be sufficiently sharp to apply at least one-hundred pounds of pressure to a patient's skin, yet not be sharp enough to pierce the patient's skin.

FIG. 8 shows a third embodiment 36 of the present invention used for partial-spine treatment and having a groove 18 with a partially arcuate configuration that closely approximates the perimeter configuration of the spinous processus of a human vertebra, such as the vertebra 24 shown in FIG. 9. Base support 12 is shown to have a greater width dimension than the height dimension of treatment member 14 to provide stable support for a patient (not shown) positioned against sharp edges 20 and 22. It contemplated for sharp edges 20 and 22 in third embodiment 36 to be filed or otherwise adapted so as to also be sufficiently sharp to apply at least one-hundred pounds of pressure to a patient's skin, yet not be sharp enough to pierce the patient's skin. FIG. 9 shows partial-spine treatment third embodiment 36 placed in its treatment position. Treatment member 14 is centrally positioned upon base support 12, with the upper portion of treatment member 14 in close proximity to the spinous processus 28 of vertebra 24. The transverse processes 26 of vertebra 24 are positioned laterally to the articular facets 38 on either side of the spinous processus 28. Although not shown, the lamina grooves on either side of the spinous processus 28 are positioned between each articular facet 38 and the spinous processus 28.

Figure 10:
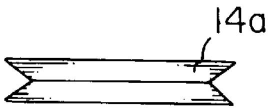
FIG. 10 is a top view of the cervical portion of the treatment member of the second embodiment of the present invention.
Figure 11:
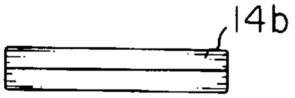
FIG. 11 is a top view of the thoracic portion of the treatment member of the second embodiment of the present invention.
Figure 12:
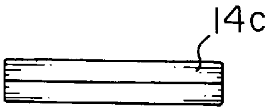
FIG. 12 is a top view of the lumbar portion of the treatment member of the second embodiment of the present invention.
Figure 13:
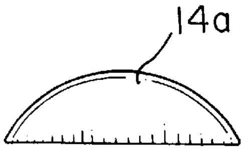
FIG. 13 is a front view of the cervical portion of the treatment member of the second embodiment of the present invention.
Figure 14:
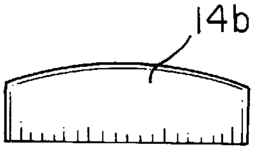
FIG. 14 is a front view of the thoracic portion of the treatment member of the second embodiment of the present invention.
Figure 15:
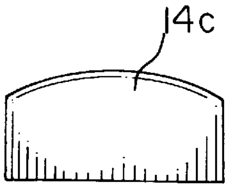
FIG. 15 is a front view of the lumbar portion of the treatment member of the second embodiment of the present invention.
Figure 16:
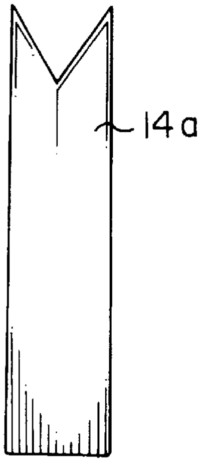
FIG. 16 is a side view of the cervical portion of the treatment member of the second embodiment of the present invention.
Figure 17:
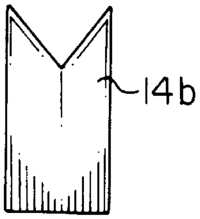
FIG. 17 is a side view of the thoracic portion of the treatment member of the second embodiment of the present invention.
Figure 18:
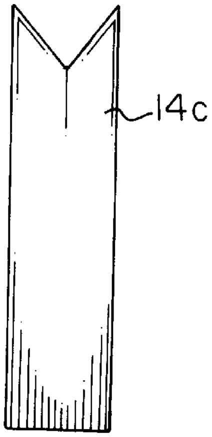
FIG. 18 is a side view of the lumbar portion of the treatment member of the second embodiment of the present invention.

FIGS. 10–18 shows the differences in treatment member 14 configuration in the cervical, thoracic, and lumbar portions of the whole-spine treatment second embodiment 34 of the present invention shown in FIG. 7. FIG. 10 shows a top view of the cervical portion of treatment member 14, designated as 14*a*, while FIGS. 11 and 12 show tops views of the thoracic and lumbar portions of treatment member 14, designated as 14*b* and 14*c*, respectively. In FIG. 10, the ends of the cervical treatment member 14*a* are shown angled inward since the ends of cervical treatment member 14*a* taper more to a point than the ends of thoracic and lumbar treatment members 14*b* and 14*c,* while in FIGS. 11 and 12 the ends of thoracic and lumbar treatment members 14*b* and 14*c* are shown as a straight line. FIG. 13 shows a front view of cervical treatment member 14*a,* while FIGS. 14 and 15 show front views of thoracic and lumbar treatment members 14*b* and 14*c,* respectively. The upper surface of cervical treatment member 14*a* shown in FIG. 13 has a higher radius of curvature than the upper surfaces of thoracic and lumbar treatment members 14*b* and 14*c,* shown in FIG. 14 and FIG. 15 respectively. The height of treatment members 14*a,* 14*b,* and 14*c* shown in FIGS. 13–15 are not to scale with respect to one another, the respective heights being more clearly shown in FIGS. 16–18. FIG. 16 shows a side view of cervical treatment member 14*a*, while FIGS. 17 and 18 show side views of thoracic and lumbar treatment members 14*b* and 14*c,* respectively. As also shown in FIG. 7, in FIGS. 16–18 cervical and lumbar treatment members 14*a* and 14*c,* respectively, are shown to have a greater height dimension than thoracic treatment member 14*b*.

The actual dimensions of base support 12 and treatment member 14 in partial-spine treatment embodiment 10 are not critical, as long as base support 12 is small enough to be easily portable and curved peripheral surface 16 of treatment member 14 is convex and has a fixed radius of curvature substantially similar to the radius of curvature of the concave portion of either a human cervical region (not shown), a human thoracic region (not shown), or a human lumbar region (not shown). The length of treatment member 14 will depend upon several factors, including the stature of the person for whom treatment is desired, whether an entire region is to be treated at once, or whether it is determined that it is more desirable to treat a spinal region in several successive treatments with a smaller treatment member 14. The present invention contemplates several sizes of partial-spine treatment embodiments 10, such as those having larger treatment members 14 for use by larger women and most men, as well as partial-spine treatment embodiments 10 having smaller treatment members 14 for use by most women and smaller men. In the preferred partial-spine treatment embodiments 10 contemplated for cervical area treatment, the smaller partial-spine treatment member 14*a* would have a length of approximately 4 inches and a radius of curvature of approximately 2½ inches, while the larger partial-spine treatment member 14*a* for cervical area treatment would have a length of approximately 5 inches, but an identical radius of curvature. Although curved peripheral surface 16 of treatment member 14*b* for thoracic region treatment would have a convex configuration that would slightly reverse the curve of the thoracic spine of a patient (not shown) lying thereupon in a supine position, in the preferred partial-spine treatment embodiments 10 for treatment of an entire thoracic region at once, it is contemplated for the smaller partial-spine treatment member 14*b* to have a length of approximately nineteen inches and a radius of curvature of approximately twelve-and-three-fourths inches, while it is contemplated for the larger partial-spine treatment member 14*b* for thoracic use to have a radius of curvature of twelve-and-one-half inches and a length of approximately twenty-two inches. Additionally, it is contemplated to have a smaller partial-spine treatment member 14*c* for lumbar region treatment which would have a length of approximately seven inches and a radius of curvature of approximately twelve-and-three-fourths inches, while it is contemplated to have a larger partial-spine treatment member 14*c* for lumbar region treatment with a radius of curvature of nine inches and an approximate length of ten inches. In the alternative, it is also contemplated in the present invention to have more compact partial-spine treatment embodiments 10 for use in treating muscles in the thoracic and lumbar regions. Each treatment member 14 would have the same radius of curvature as noted above, but would have a shorter length dimension of approximately six inches. Thus, with the more compact partial-spine treatment embodiments 10 contemplated, treatment of a thoracic or lumbar region would be accomplished in several successive treatment sessions instead of a single session, and preferably such treatments would be accomplished with a patient sitting in a chair or against another type of rigid support surface. Further, the dimensions for a smaller whole-spine treatment device 34 would be the collective dimensions of three smaller partial-spine treatment members 14*a,* 14*b,* and 14*c,* while the dimensions for a larger whole-spine treatment device 34 would be the collective dimensions of three larger partial-spine treatment members 14*a,* 14*b,* and 14*c.*

To use the present invention, either partial-spine treatment embodiment 10 or whole-spine treatment embodiment 34 would be placed with base supports 12 and 12' positioned against a flat surface (not shown) and treatment members 14 and 14' upwardly depending respectively therefrom. A patient (not shown) would then be positioned so that the spinous processus of each vertebra of the spinal region to be treated is substantially contained within groove 18 or 18' in the top portion of treatment member 14 or 14' respectively. With a patient in such a position, sharp edges 20 and 22, as well as 20' and 22', will apply deep concentrated pressure to muscle attachments, such as attachments of muscles 32*a*–32*e* shown in FIGS. 4–6, in the lamina groove on either side of the spinous processes of the spinal vertebrae, to lengthen them for automatic vertebra realignment as a result of such lengthening, as well as elimination of pain previously associated with the treated area due to any excess muscle contraction. It is contemplated for the patient to remain positioned against sharp edges 20 and 22, and also sharp edges 20' and 22', for periods of time not exceeding ten minutes. Relief of pain and increased mobility will often immediately follow muscular therapy treatment. Use of partial-spine treatment embodiment 10 and whole-spine treatment embodiment 34 duplicates manual muscular therapy treatments performed by muscular therapist hands (not shown) on a patient's spine and thereby reduces the overall risk of injury to muscular therapists from repeated application of over one-hundred pounds of concentrated pressure to muscular tissues which can be required to lengthen deeper back muscles. Use of the present invention does not reduce the quality of treatment provided to patients, and it enables patients to administer uniform and effective self-treatment to muscles attached in the lamina grooves on either sides of their spinous processes.

What is claimed is:

1. A device for applying concentrated pressure to muscles attached in the lamina groove on either side of the spinous processes in the cervical, thoracic, and lumbar regions of a human spine, which simulates the type of deep concentrated pressure applied by muscular therapist hands to the seven layers of muscles attached in the lamina groove to lengthen the attachments of even the innermost of said seven muscles for automatic vertebrae alignment as a result of such lengthening, as well as increased flexibility and elimination of pain previously associated with the region treated resulting from excess muscle contraction, said device comprising a rigid planar base member having an upper surface;

a rigid treatment member upwardly depending from said upper surface, said treatment member also having an arcuate peripheral surface, a groove longitudinally oriented in said peripheral surface, and a pair of sharp edges positioned on either side of said groove, said groove having maximum depth and width dimensions of approximately one-half inch so that said sharp edges can support a patient in the lamina groove immediately on either side of the spinous processes when a patient is positioned against said peripheral surface and said sharp edges are thereby able to cause uniformly deep concentrated pressure in excess of one-hundred pounds of pressure to be applied to the seven layers of muscles attached in the lamina groove on either side of the spinous processes to cause the muscles to relax and lengthen and thereby provide vertebrae alignment without any forcing of bone.

2. The device of claim 1 wherein said arcuate peripheral surface has an essentially convex configuration conforming to the concave curvature of the cervical region of a human spine.

3. The device of claim 2 wherein said arcuate peripheral surface has a length dimension of approximately four inches and a radius of curvature of approximately two-and-one-half inches to support the cervical region of a smaller human spine.

4. The device of claim 2 wherein said arcuate peripheral surface has a length dimension of approximately five inches and a radius of curvature of approximately two-and-one-half inches to support the cervical region of a larger human spine.

5. The device of claim 1 wherein said arcuate peripheral surface has a convex configuration conforming to the concave curvature of the thoracic region of a human spine.

6. The device of claim 5 wherein said convex configuration of said arcuate peripheral surface essentially conforms to said concave curvature of the thoracic region of a human spine, while at the same time slightly reversing said concave curvature in the thoracic region of a patient lying upon said curved peripheral surface.

7. The device of claim 5 wherein said arcuate peripheral surface has a length dimension of approximately nineteen inches and a radius of curvature of approximately twelve-and-three-fourths inches to support the thoracic region of a smaller human spine.

8. The device of claim 5 wherein said arcuate peripheral surface has a length dimension of approximately twenty-two inches and a radius of curvature of approximately twelve-and-one-half inches to support the thoracic region of a larger human spine.

9. The device of claim 1 wherein said arcuate peripheral surface has a convex configuration conforming to the concave curvature of the lumbar region of a human spine.

10. The device of claim 9 wherein said arcuate peripheral surface has a length dimension of approximately seven inches and a radius of curvature of approximately twelve-and-three-fourths inches to support the lumbar region of a smaller human spine.

11. The device of claim 9 wherein said arcuate peripheral surface has a length dimension of approximately ten inches and a radius of curvature of approximately nine inches to support the lumbar region of a larger human spine.

12. The device of claim 1 wherein said arcuate peripheral surface has a convex configuration conforming to the combined concave curvature of the cervical, thoracic, and lumbar regions of a human spine.

13. The device of claim 12 wherein said convex configuration essentially conforms to said concave curvature of the thoracic region of a human spine, while at the same time slightly reversing said concave curvature in the thoracic region of a patient lying on top of said curved peripheral surface.

14. The device of claim 12 wherein said base member and said treatment member each have a length dimension and said length dimension of said base member is greater than said length dimension of said treatment member, and wherein said base member also has an upper edge and said treatment member has an upper end, and wherein said treatment member is placed in a non-centered position against said base member with said upper end adjacent to said upper edge.

15. The device of claim 12 wherein said base member has a total length dimension and a lower end having a length dimension approximately one-third of said total length dimension, and further wherein said lower end has a greater thickness dimension than the remainder of said base support.

16. The device of claim 1 wherein said base support and said treatment member are made as a one-piece unit with molded construction.

17. The device of claim 1 wherein said groove has straight interior walls set apart at and angle approximately between 60° and 70°.

18. The device of claim 1 wherein said groove has an arcuate configuration slightly larger than the spinous processus intended for receipt therein, and wherein said arcuate configuration closely complementing the curvature of the spinous processus it is intended to receive.

19. A method for simultaneously applying concentrated pressure to the seven layers of muscles attached in the lamina groove on either side of the spinous processes of the vertebrae in the cervical, thoracic, and lumbar regions of a human spine, the type of concentrated pressure which simulates the type of deep pressures applied by muscular therapist hands to spine muscles to lengthen them for increased patient flexibility, automatic vertebrae alignment as a result of such lengthening, and elimination of pain previously associated with the region treated as a result of excess muscular contraction, said method comprising the steps of providing a rigid planar base member with an upper surface and a rigid treatment member;

attaching said treatment member to said upper surface of said base member so that said treatment member upwardly depends from said upper surface;

forming the peripheral surface of said treatment member into a convex surface which essentially conforms to the concave curvature of a human spine;

forming a longitudinally oriented groove that is essentially V-shaped and has maximum depth and width dimensions of approximately one-half inch into said peripheral surface while also forming a pair of sharp edges in said peripheral surface on either side of said groove which are sufficiently sharp to apply one-hundred pounds of pressure against a patient's skin but not sufficiently sharp to pierce the patient's skin; and positioning a patient against said peripheral surface so that said peripheral surface supports a patient immediately in the lamina groove on both sides of the spinous processus of each supported vertebra, with said spinous processes being received within said groove and said sharp edges uniformly and deeply applying concentrated pressure to muscles in the treated region that are attached in the lamina grooves on either side of the spinous processes to relax and lengthen the muscles to cause alignment of vertebrae without the forcing of bone.

20. The method of claim 19 wherein said step of positioning a patient against said peripheral surface is selected from a group consisting of placing the patient in a supine position over said peripheral surface so that the region of the patient to be treated rests upon said peripheral surface; placing the patient in a chair having a back member with the peripheral surface between the back member of the chair and the region of the patient to be treated; and placing the patient in front of an upright rigid support surface larger than said peripheral surface with said peripheral surface positioned between the upright rigid support surface and the region of the patient requiring treatment.

* * * * *